United States Patent
Pasch

(10) Patent No.: US 6,211,517 B1
(45) Date of Patent: Apr. 3, 2001

(54) ELECTRON BEAM FAULT DETECTION OF SEMICONDUCTOR DEVICES

(75) Inventor: Nicholas F. Pasch, Pacifica, CA (US)

(73) Assignee: LSI Logic Corporation, Milpitas, CA (US)

( * ) Notice: Subject to any disclaimer, the term of this patent is extended or adjusted under 35 U.S.C. 154(b) by 0 days.

(21) Appl. No.: 09/088,801

(22) Filed: Jun. 2, 1998

(51) Int. Cl.[7] .............................. H01J 37/16; H01J 37/26
(52) U.S. Cl. ...................................... 250/310; 357/441.11
(58) Field of Search .............................. 250/441.1, 310, 250/306, 397, 492.1, 492.21, 442.11

(56) References Cited

U.S. PATENT DOCUMENTS

| | | | |
|---|---|---|---|
| 3,772,520 | * 11/1973 | Varker | 250/307 |
| 4,560,880 | * 12/1985 | Petric et al. | 250/441.1 |
| 4,584,479 | * 4/1986 | Lamattina et al. | 250/441.1 |
| 4,607,167 | * 8/1986 | Petric | 250/492.2 |
| 5,360,988 | 11/1994 | Uda et al. | 257/529 |
| 5,521,516 | 5/1996 | Hanagama et al. | 324/751 |
| 5,583,344 | * 12/1996 | Mizumura et al. | 250/492.21 |
| 5,867,547 | * 2/1999 | Lee | 376/204 |

* cited by examiner

*Primary Examiner*—Bruce C. Anderson

(57) ABSTRACT

An E-beam generator and detector arrangement sends an electron beam through a series of differentially evacuated vacuum chambers of small size to detect faulty circuitry in individual semiconductor devices. The vacuum chambers are open to one end and are sealed by the semiconductor device without contacting the vacuum chambers. A laser generator is operated by a control system with the E-beam generator and detector arrangement to provide a laser beam in a known physical relationship to the electron beam to correct detected faulty circuitry in the semiconductor devices. The E-beam generator and detector arrangement confirms the correction without further handling of the semiconductor device.

10 Claims, 1 Drawing Sheet

ELECTRON BEAM FAULT DETECTION OF SEMICONDUCTOR DEVICES

TECHNICAL FIELD

The present invention relates generally to semiconductor manufacturing technology and more specifically to electron beam fault detection and laser fault correction of circuitry in semiconductor devices.

BACKGROUND ART

Fairly complex electronic circuits are very difficult to test. Currently, it is not possible to stimulate a semiconductor device from its perimeter pads with the one-hundred percent confidence that every single node of the device will be exercised. Generally, the best fault coverage (the number of nodes testable divided by the number of nodes total) is around 90 to 95 percent. And, even with the best fault coverage, there is still a significantly non-negligible probability that although the device may pass the fault screening that it still may not work.

One of the historical difficulties has been that there is a limited amount of surface area on the perimeter of a given device. Since most of the perimeter surface area for complex electronic circuits is used for pads required for operation of the device, very little perimeter space can be allocated strictly for fault detection purposes. In designing semiconductor devices, it has always been desirable but not feasible to provide for additional test pads to be used to probe and interrogate all the nodes including those normally not interrogated which are internal to the device.

A new problem which is starting to arise is that RAM is being incorporated in greater amounts in complex logic circuits. It is not possible to have enough perimeter pads to test the high density RAM with the number of pads required for the complex logic circuitry. It is, however, possible to test using circuitry incorporated in the device itself, but the results of the fault detection must still be made available to the outside through additional pads.

An interesting alternative has been to include circuitry to test the RAM and instruct the RAM to repair itself using a number of different mechanisms. The mechanisms used would depend on where the fault is located and its nature. However, it is still necessary to be able to known, outside the device, the number and nature of the self-repairs in order to control the quality of the manufacturing process. It may well be that the problems which are being self-repaired are those which should be prevented by changes in the manufacturing process rather than through fault detection. This would result in a higher reject rate, or lower yield, than necessary. In any event, additional perimeter pads are still required to bring the information to the outside.

Another minor problem which existed in the prior art is that the temperature at which the tests are run will not necessarily correspond to the temperature at which a device will operate. Thus, while the device would pass the probe tests, this would be no assurance that the device would operate properly in actual operation.

One solution to the above involves electron beam (E-beam) probing. E-beam probing is well known in the fault detection field where a primary electron beam irradiates locations on a semiconductor and secondary electron emissions from the locations are measured to determine the potential at such locations.

In this solution, E-beam probing is coupled with non-perimeter test pads. The surface area test pads are incorporated into the layout of the device die to propagate upward through the structure of the device die from particular nodes to the top layer of the die under the passivation layer. Electron beams played on the surface of operating die are able to probe at the test pad locations for various potentials. This is especially true when the device is put into a characterized state. The characterized state is defined as where the device is powered and the input/output convention is specified; it is not necessary that the device be clocked at full operating speed.

While the above is an elegant solution, it has a number of drawbacks. The one major problem is that an electron beam will only work in a relatively hard vacuum. This means that testing of wafers or die must be done in a vacuum chamber large enough to contain the wafers or die. This requirement of a large vacuum chamber means a great deal of time is required to pump down to the hard vacuum, approximately $10^{-6}$ torr at which the electron beam will operate. This slows the processing of wafers and die significantly.

This solution has the attendant problem of requiring additional handling for the devices in and out of the vacuum chamber and resultant breakage.

Another problem is that each different semiconductor device requires a custom probe pad system for establishing the characterize state in the particular device. Still further, the custom probe pad system must be capable of working in a hard vacuum and there must be an arrangement for wiring out the custom probe pad systems to the outside of the vacuum chamber to the control system.

Another problem resulting from testing, followed by correction, followed by testing is that the test probe wires make an indentation on initial contact with the test pads which may cause problems on a second contact. Thus, although a correction is made, the second testing may have false errors introduced by the second testing itself.

A solution for solving these various problems has been long sought by but elusive to those skilled in the art.

DISCLOSURE OF THE INVENTION

The present invention provides for fault detection for semiconductor devices in wafers, die, or partially packaged form in a continuous processing mode using an electron beam in a vacuum obtained by differentially-pumped chambers of less-than-device-size.

An advantage of the present invention is to provide a continuous fault detection system for semiconductor devices which does not require time consuming vacuum pump downs.

A further advantage of the present invention is to provide a fault detection system which does not require custom probe pad systems which are operable in a hard vacuum.

An even further advantage of the present invention is to provide a continuous fault correction system for semiconductor devices which does not require time consuming vacuum pump downs.

An even further advantage of the present invention is to provide a unified system for fault detection for semiconductor devices where the device does not have to be removed from the system for testing, for fault correction and then retesting.

The above and additional advantages of the present invention will become apparent to those skilled in the art from a reading of the following detailed description when taken in conjunction with the accompanying drawings.

BEST MODES FOR CARRYING OUT THE INVENTION

Figure 1:
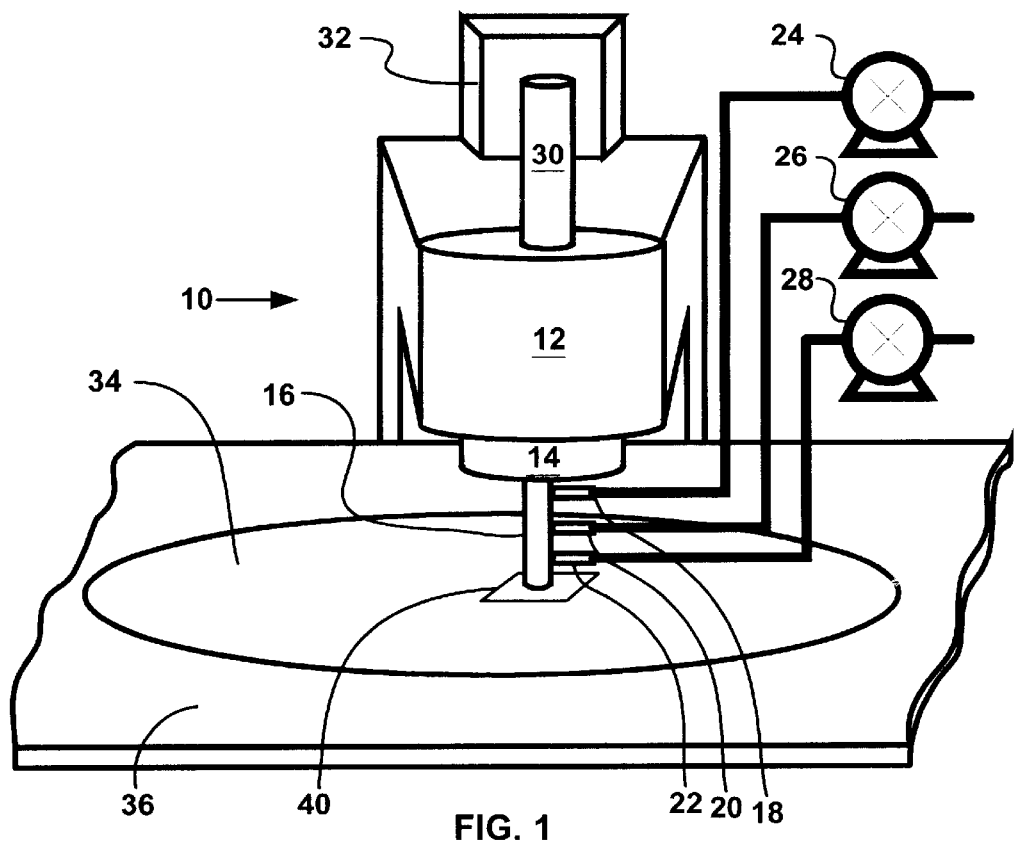
FIG. 1 is a isometric drawing of the system, partially in schematic form, of the present invention used in fault detection and fault correction of semiconductor devices on a silicon wafer.

Referring now to FIG. 1, therein is shown the electron beam fault detection and laser fault correction system 10. The system 10 includes an electron beam (E-Beam) generator 12 connected to an E-beam/laser director/detector 14 which contains electron optics for directing the electron beam, laser optics for directing the laser beam, and a detector for detecting secondary electrons.

Due to the small size of the components of the present invention, the electron optics can be electrostatic optics in addition to electromagnetic optics which are conventionally used.

The E-beam/laser director/detector 14 is connected to a series of vacuum chambers, collectively designated as vacuum chambers 16, of which only the outer vacuum chamber is shown. The vacuum chambers 16 are connected to an outer port 18, a middle port 20 and an inner port 22. The outer port 18 is connected to a soft vacuum pump 24. The middle port 20 is connected to an intermediate vacuum pump 26. And, the inner port 22 is connected to a hard vacuum pump 28.

Associated with the E-beam generator 12 is a laser generator 30. For purposes of illustration only, the laser generator 30 is shown slightly offset from the E-beam generator 12. As will hereinafter be explained, the physical relationship between the E-beam generator 12 and the laser generator 30 is flexible as long as the relationship is known. The control system 32 is shown disposed on the support for the E-beam generator 12.

The control system 32 contains the circuitry for controlling the movement of the wafer carrier 36 and the E-beam generator 12 and laser generator 30 combination. The control system 32 also controls the various vacuum pumps as well as the circuitry for putting the portion of a wafer 34 which contains an integrated circuit chip, or semiconductor device 40, into its characterize state and performing the other procedures associated with conventional fault detection. The control system 32 is a microprocessor-based system.

The E-beam generator 12 and the laser generator 30 are above and movable with respect to the semiconductor devices on the semiconductor wafer 34. In fact, the degree of movement of the E-beam generator 12 and the laser generator 30 are sufficiently fine that the vacuum chambers 16 can be moved to a plurality of positions over a single semiconductor device. The semiconductor wafer 34 is in the wafer carrier 36 which is movable with respect to the system 10 in the X-Y-Z directions. The wafer carrier 36 has wafer-shaped recesses (only one shown) into which the semiconductor wafer 34 is inserted such that the surfaces of the semiconductor wafer 36 and the wafer carrier 36 will be coplanar.

Figure 2:
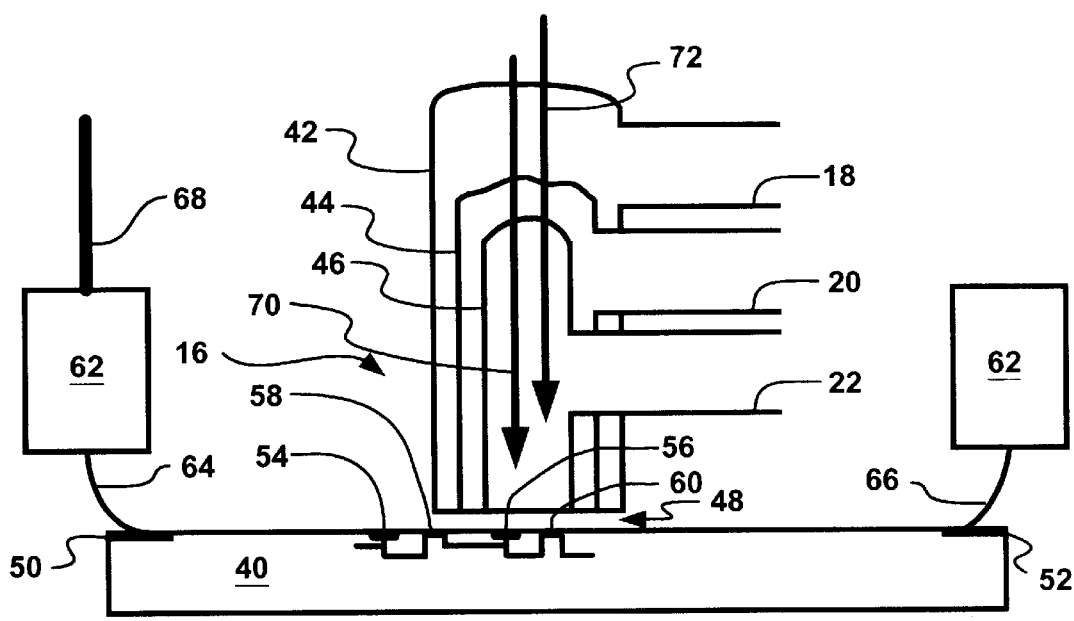
FIG. 2 is a schematic, partially in section, of the present invention used in fault detection and correction of a semiconductor device on a die.

Referring now to FIG. 2, therein is shown a close up, not-to-scale, illustration of the present invention in which the vacuum chambers 16 are small enough or necked down enough to cover small portions of an individual semiconductor device 40. The vacuum chambers 16 would only be centimeters in length and millimeters in diameter overall. The vacuum chambers 16 consist of three chambers. An outer vacuum chamber 42 is open to the bottom and is connected to the outer port 18. A middle vacuum chamber 44 is open to the bottom and is connected to the middle port 20. And an inner vacuum chamber 46 is open to the bottom and is connected to the inner port 22. FIG. 2 shows the vacuum chambers 16 and ports in section. Only the inner chamber 46 needs to be open at the top to connect to the E-beam generator 12. The other chambers could be welded to the inner chamber 46. From FIG. 1, it is seen that the outer port 18, the middle port 20, and the inner port 22 would be respectively connected to the soft vacuum pump 24, the intermediate vacuum pump 26 and the hard vacuum pump 28.

The open ends of the vacuum chambers 16 are separated from the semiconductor device 40 by a gap 48 which is shown exaggerated in FIG. 2. The semiconductor device 40 has a series of input/output pads around its outer perimeter such as I/O pads 50 and 52. Within the perimeter of the semiconductor device 40 are a series of test pads, exemplified by test pads 54 and 56 which bring up the potentials at various nodes buried within the body of the semiconductor device 40. Connected to the various nodes are a series of fuses, exemplified by fuses 58 and 60, which will isolate various faulty circuits in the semiconductor 40 when they are cut. This form of fault correction is most typical for RAM cells.

Spaced a short distance from the semiconductor device 40 is a probe frame 62 from which extend a number of tungsten probe wires, such as probe wires 64 and 66, which would contact the I/O pads 50 and 52, respectively. The probe frame 62 has a connector 68 which connects the control system 32 shown in FIG. 1 to the various tungsten probe wires. It should be noted that this probe frame 62 and the connector 68 are located outside of the vacuum chambers 16 and thus do not have to be set up for operation in a vacuum. Further, the probe frame 62 is held by a conventional probe frame support (not shown) so that it can be moved up and down to bring it into contact with the semiconductor devices as the wafer 34 is stepped below it. The probe frame 62 is not shown in FIG. 1 for purposes of clarity. It should be recognized that the vacuum chambers 16 are small enough to be moved by the system 10 within the probe frame 62 to position the electron beam over substantially all the surface area of the semiconductor device 40.

Also shown in FIG. 2 are arrows 70 and 72 which designate the directions of the energy beams which affect the semiconductor device 40. For fault detection, it would be the beam 70 of electrons and for the fault correction, it would be the beam 72 of laser light. In FIG. 2, one is shown adjacent and slightly offset from the other such that the beam of electrons 70 would be the targeting mechanism and the beam 72 of laser light would be the mechanism for making corrections.

Although the beams are shown adjacent and slightly offset in FIG. 2, it is only necessary that the relationship between the two beams 70 and 72 be known. For example, the two beams 70 and 72 could be widely separated with the laser beam 72 going through outer vacuum chamber 42, the middle vacuum chamber 44, or even outside the vacuum chambers 16. The present invention even contemplates the possibility of fault detection on one wafer and the correction on another wafer as long as the semiconductor devices do not have to be handled between fault detection and correction.

In operation as shown in FIG. 1, the wafer carrier 36 places the wafer 34 under the electron beam fault detection and laser fault correction system 10. There is a space, or gap 48, of approximately 20 microns or less between the bottom of the vacuum chambers 16 and the surface of the wafer 34 as shown in FIG. 2. The vacuum pumps 24, 26, and 28 are then either started or continue running to evacuate the vacuum chambers 16. Each draws a different hardness of vacuum such that a relatively soft vacuum is created in the outer chamber 42 between it and the middle chamber 44. A slightly harder vacuum is created between the middle chamber 44 and the inner chamber 46.

The vacuum inside the inner chamber 46 is described as hard since it will be a vacuum sufficiently hard for proper operation of an electron beam. With current E-beam equipment, the hardness of vacuum would need to be in the order of $10^{-6}$ torr. It should be noted that with the small gap of approximately 20 microns or less, there will be an effective seal between the outside ambient air and the inside of the inner chamber 46. Further, due to the small size of the vacuum chambers 16, the vacuum chambers 16 could be pumped down in a couple of seconds.

Even when the wafer 34 is moved out from under the vacuum chambers 16, since the surfaces of the semiconductor wafer 34 and the wafer carrier 36 are coplanar, the differential vacuums will be maintained. Any air brought in between the perimeters of the semiconductor wafer 34 and the wafer carrier 36 would be removed in fractions of a second.

As would be evident to those skilled in the art, even harder vacuums or larger gaps would be possible by adding additional outer chambers with evacuation to intermediate hardness vacuums. The concept is to have differential vacuums from the outside atmosphere to the inner chamber 46 so as to reduce the air flow due to the constant leakage of air between the openings and the semiconductor wafer 34 or the wafer carrier 36. Similarly, it would be evident to those skilled in the art that a single multi-stage pump capable of pumping different levels of vacuum could be utilized. One particular approach of an alternate embodiment is the use of a single vacuum pump with vacuum relief valves in the lines from ports 18 and 20 to replace the separate pumps 24, 26, and 28 as long as the differential levels of vacuum could be obtained.

Once the inner chamber 46 attains the necessary vacuum, the control system 32 will provide signals to the tungsten wires 64 and 66 necessary to put the semiconductor device 40 into its characterize state.

The electron beam generator 12 is then turned on to provide the beam of electrons through the E-beam/laser director/detector 14 which directs the primary electron beam to different areas of the surface of the semiconductor device 40. The E-beam/laser director/detector 14 also includes the detectors which sense secondary electron emissions from the irradiation of the primary electrons on the semiconductor device 40 within the inner chamber 46. This arrangement makes it possible to determine the potential at an individual selected surface test pad 54.

It is also possible to determine if the primary electron beam is irradiating a test pad 54 or a non-test pad area. The control system 32 is responsive to the irradiation of a non-test pad area to move the wafer carrier 36 to move the wafer 34 and the semiconductor device 40 into the correct alignment for fault detection only at test pad areas. If the correct alignment is very small, the control system 32 would move the system 10 or redirect the primary electron beam with the electrostatic optics. Effectively, the electron beam provides a system of self alignment of the semiconductor device 40 for probe testing. It should be understood that this is a significant advantage of the present system in that good devices have sometimes been discarded merely because the probe testing was done on the wrong location of the semiconductor device.

When the system 10 determines that the correct potential exists in the proper location at test pad 54, it then proceeds to the next test pad 56. If the potential is incorrect, for example at test pad 54, then the control system 32 has the laser generator 30 provide a laser beam. The laser optics in the E-beam/laser director/detector 14 directs the laser beam to cut a fuse, for example at fuse 60, to cut the faulty cell or circuitry away from the faultless circuitry and thereby correct the fault.

Finally, the system 10 can then recheck to confirm that the potential at the test pad 54 is correct. The great advantage of this approach is that the probe frame 62 does not have to be moved during the entire testing, correction and retesting. Thus, the I/O pads 50 and 52 will not have repeated contacts with the tungsten wires 64 and 66.

Since the vacuum chambers 16 have a small but finite size, it will be realized that the vacuum chambers 16 cannot be moved to provide the electron and laser beams to the entire surface area of a semiconductor device 40 when the probe frame 62 is in place. This can be corrected for in the design of the semiconductor 40 itself by placing all the test pads in locations where access is possible.

The energy in the laser would also help to clean the E-beam/laser director/detector 14 of contaminants deposited on the internal components due to the E-beam acting on matter, such as vacuum pump lubricants, in the inner chamber 46. At the same time, the vacuum pumping of the inner chamber 46 would remove residue from the lasing from the target area and avoid polluting the atmosphere.

After the correction of the fault, the wafer carrier 36 would then move another test pad on the semiconductor device 40 under the operative portion of the system 10.

For fault correction, it would be realized by those skilled in the art that the vacuum chambers 16 are desirable but not essential. It is novel to have the fault correcting laser beam 72 operating in conjunction with the fault detection.

It should be noted that with an electron beam, it is also possible to impose potentials on test pads and determine if the potentials are maintained or lost due to opens or shorts in the circuitry. This means that the system is capable of operating on a die before the perimeter pads are put in place or without the semiconductor device 40 being in the characterize state.

While not currently possible with previously existing technology, wafers can be tested using the present invention in intermediate steps during processing. Process control monitoring is now possible at the individual transistor or other component level after source/drain implantation to test basic device parameters. This would save time and money because improper processing could be identified before all the steps of processing were completed. This would be especially advantageous during manufacturing process debugging. Currently, complex processes have two month turn around times from the start to end of processing so anything which can detect problems through the cycle would greatly reduce cost and decrease the time required for trouble shooting of semiconductor devices.

Once the testing is complete on all the semiconductor devices 40 on the wafer 34, the wafer carrier 36 will move to the next wafer. In moving past the vacuum chambers 16, the wafer carrier 36 will provide a substantially continuous surface for maintaining the seal of the vacuum chambers 16. Where the wafer carrier 36 contains a plurality of wafers, the next wafer can be put into place with a minimal loss of the various vacuums in the vacuum chambers 16. This would permit continuous processing of wafers.

In operation as shown in FIG. 2, an individual semiconductor device 40 in its own wafer carrier or a lidded, packaged device could also be tested. The former might be used during military specification qualification of specific devices and the latter to detect high temperature die attach problems or during failure analysis of returned devices.

The system 10 is different from the systems used in the past which required one system for fault detection and an entirely separate one for fault correction with handling and tracking systems in between.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations which fall within the spirit and scope of the appended claims. All matters set forth herein or shown in the accompanying drawings are to be interpreted in an illustrative and non-limiting sense.

The invention claimed is:

1. Apparatus for fault detection in semiconductor devices, comprising:

an electron beam generator and secondary electron detector arrangement requiring a vacuum to operate;

a first chamber open at one end and connected to said electron beam generator and secondary electron detector at the other;

a second chamber disposed around said first chamber and open at one end;

a first pump mechanism connected to said second chamber for evacuating said second chamber;

a second pump mechanism connected to said first chamber for evacuating said first chamber to the vacuum required by said electron beam generator and detector arrangement to operate and a harder vacuum than in said second chamber;

a semiconductor device carrier for movably positioning the semiconductor device in close proximity with said open ends of said first and second chambers whereby the semiconductor device seals said first and second chambers without contacting said open ends of said first and second chambers;

a control system for placing the semiconductor device in a characterize state; and said control system including a probe pad system connecting said control system with the semiconductor device, said probe pad system being disposed outside said second chamber around the perimeter of the semiconductor device whereby said control system places the semiconductor device in the characterize state through said probe pad system.

2. The apparatus as claimed in claim 1 including:

a third chamber open at one end and disposed around said second chamber; and a third pump mechanism for evacuating said third chamber to a softer vacuum than in said first and second chambers.

3. The apparatus as claimed in claim 1 wherein said openings of said first and second chambers are smaller than the semiconductor device.

4. The apparatus as claimed in claim 1 wherein said second pump mechanism is capable of evacuating said first chamber to approximately $10^{-6}$ torr.

5. The apparatus as claimed in claim 1 wherein said openings of said first and second chambers are spaced approximately 20 microns from said semiconductor device carrier.

6. The apparatus as claimed in claim 1 wherein:

said second pump mechanism is a pump; and said first pump mechanism is a vacuum relief valve.

7. The apparatus as claimed in claim 1 wherein said electron beam generator and detector arrangement is capable of imposing potentials on an area of the semiconductor device for fault detection and determining the potential on said area after imposing said potential.

8. Apparatus for fault detection is semiconductor devices, comprising:

an electron beam generator and secondary electron detector arrangement requiring a vacuum to operate;

a first chamber open at one end and connected to said electron beam generator and secondary electron detector at the other;

a second chamber disposed around said first chamber and open at one end;

a first pump mechanism connected to said second chamber for evacuating said second chamber;

a second pump mechanism connected to said first chamber for evacuating said first chamber to a harder vacuum than said second chamber;

a third chamber open at one end and disposed around said second chamber;

a third pump mechanism for evacuating said third chamber to a softer vacuum than in said first and second chambers whereby a vacuum is provided for operation of said electron beam generator and secondary electron detector arrangement; and a semiconductor device carrier for positioning the semiconductor device in close proximity with said open ends of said first and second chambers whereby the semiconductor device seals said first, second, and third chambers without contacting said open ends of said first, second, and third chambers;

a control system for providing signals to place the semiconductor device in a characterize state; and said control system including a probe pad system connecting said control system with the semiconductor device, said probe pad system being disposed outside said second chamber around the perimeter of the semiconductor device whereby said control system places the semiconductor device in the characterize state through said probe pad system.

9. The apparatus as claimed in claim 8 wherein the open end of said third chamber is smaller than the semiconductor device.

10. The apparatus as claimed in claim 8 wherein the vacuums hardens from said third chamber to said second chamber to said first chamber and the vacuum in said first chamber is approximately $10^{-6}$ torr in operation.

* * * * *